United States Patent
Ohki

(10) Patent No.: US 8,376,935 B2
(45) Date of Patent: Feb. 19, 2013

(54) OBSERVED IMAGE FORMING APPARATUS

(75) Inventor: Toshio Ohki, Saitama (JP)

(73) Assignee: FUJINON Corporation, Saitama-shi (JP)

( * ) Notice: Subject to any disclaimer, the term of this patent is extended or adjusted under 35 U.S.C. 154(b) by 1180 days.

(21) Appl. No.: 12/200,493

(22) Filed: Aug. 28, 2008

(65) Prior Publication Data

US 2009/0076327 A1 Mar. 19, 2009

(30) Foreign Application Priority Data

Sep. 19, 2007 (JP) ................. P2007-241763

(51) Int. Cl.
*A61B 1/00* (2006.01)
*A61B 1/04* (2006.01)

(52) U.S. Cl. .................. 600/132; 600/134; 600/109

(58) Field of Classification Search .............. 600/110, 600/113, 118, 132, 134
See application file for complete search history.

(56) References Cited

U.S. PATENT DOCUMENTS

| | | | |
|---|---|---|---|
| 4,407,272 A * | 10/1983 | Yamaguchi | 600/109 |
| 4,433,675 A * | 2/1984 | Konoshima | 600/178 |
| 4,853,774 A | 8/1989 | Danna et al. | |
| 4,855,819 A * | 8/1989 | Hibino et al. | 348/70 |
| 4,860,094 A | 8/1989 | Hibino et al. | |
| 5,540,683 A * | 7/1996 | Ichikawa et al. | 606/40 |
| 5,554,893 A | 9/1996 | Oku | |
| 6,327,493 B1 * | 12/2001 | Ozawa et al. | 600/476 |
| 6,872,207 B2 * | 3/2005 | Ohyama et al. | 606/46 |
| 7,766,905 B2 * | 8/2010 | Paterson et al. | 606/34 |
| 2005/0065402 A1 * | 3/2005 | Moriyama et al. | 600/133 |
| 2009/0015418 A1 * | 1/2009 | Koike | 340/636.1 |
| 2009/0024771 A1 * | 1/2009 | Koike et al. | 710/18 |

FOREIGN PATENT DOCUMENTS

| | | |
|---|---|---|
| EP | 0 061 748 A1 | 10/1982 |
| EP | 1 600 101 A2 | 11/2005 |
| JP | 2-271823 A | 11/1990 |
| JP | 9-308606 A | 12/1997 |
| JP | 2004-236738 A | 8/2004 |

* cited by examiner

*Primary Examiner* — Philip R. Smith
*Assistant Examiner* — William Chou
(74) *Attorney, Agent, or Firm* — Birch, Stewart, Kolasch & Birch, LLP

(57) ABSTRACT

An observed image forming apparatus comprises: an apparatus body including a plurality of connector receivers to which electric connectors of a plurality of observation devices for obtaining an image of an object to be observed can be connected; a cap that is to be mounted to one of said plurality of connector receivers to which any of said plurality of electric connectors is not connected; and a cap insertion and extraction detecting circuit that detects whether or not the cap is mounted to the one of the connector receivers in the apparatus body, wherein, when mounting of the cap has been detected by the cap insertion and extraction detecting circuit, one of the observation devices an electric connector of which is connected to the other one of the connector receivers in the apparatus body is controlled to be driven.

2 Claims, 4 Drawing Sheets

US 8,376,935 B2

OBSERVED IMAGE FORMING APPARATUS

BACKGROUND OF THE INVENTION

1. Field of the Invention

The present invention relates to an observed image forming apparatus, and more particularly, to a structure of an electronic endoscope apparatus or a complex observation apparatus provided with a plurality of connector receivers for connecting a plurality of observation devices by way of connectors, wherein a cap is mounted to the connector receiver to which the observation device is not connected.

2. Description of the Related Art

The electronic endoscope apparatus can display an image of an object to be observed on a monitor, by taking an image of the object to be observed by a CCD (Charge Coupled Device) which is a solid body photographing element mounted on a scope (an electronic endoscope) for example, by supplying an image taking signal from this CCD to a processor unit, and by performing a determined process on the signal in an image processing circuit in this processor unit. The electronic endoscope apparatus of this type is so constructed that a plurality of scopes having different types of the CCD and different image taking systems can be connected to the processor unit. There is also a complex observation apparatus which is so constructed that as well as the aforesaid scopes, ultrasonic probes for taking ultrasonic images can be connected thereto. With this complex observation apparatus, it is possible to display and observe both an electronic endoscope image and an ultrasonic image.

In FIGS. 5A and 5B, there is shown a structure of the related-art electronic endoscope. As shown in FIG. 5A, in an electronic endoscope 1A of type A, for example, an optical connector 3 and an electric connector 4a in a square shape are connected to a processor unit 2. With this optical connector 3, a light guide for supplying light of a light source into the electronic endoscope 1A, as an illumination light is connected to the processor unit 2. The electric connector 4a is provided for the purpose of connecting a signal line for mainly transmitting an image signal and so on which has been obtained by the CCD or the like mounted on the electronic endoscope 1A, to the processor unit 2.

Moreover, as shown in FIG. 5B, in an electronic endoscope 1B of type B, for example, the optical connector 3 and an electric connector 5a in a round shape are connected to the processor unit 2. On the other hand, the processor unit 2 is provided with a connector receiver 4b in a square shape which is fit for the electric connector 4a in a square shape of the electronic endoscope 1A of type A, and a connector receiver 5b in a round shape which is fit for the electric connector 5a in a round shape of the electronic endoscope 1B of type B. In other words, in the related-art case, the two connector receivers 4b, 5b are provided corresponding to two types of the electronic endoscopes 1A and 1B. Because shapes of the electric connectors 4a, 5a are different in type A and in type B, image processing or so which is suitable to respective types of the electronic endoscopes 1A, 1B can be performed, while avoiding erroneous connection of the connectors.

By the way, in the related-art electronic endoscope apparatus, in case where the connector is connected to one of the connector receivers 4b, 5b, and the other connector receiver is exposed, as shown in FIGS. 5A and 5B, water content may intrude into the connector receiver 4b, 5b during use of the apparatus, and electrical safety may be deteriorated. At the same time, a trouble may occur in circuit operation inside the processor unit 2, in some cases. Moreover, such possibility that a user of the like may get in touch with electrodes such as pins inside the connector receivers 4b, 5b cannot be denied.

Under the circumstances, caps 4c, 5c adapted to be mounted and dismounted to and from the connector receivers 4b, 5b have been provided in the related art, as shown in FIGS. 5A and 5B. Specifically, the caps 4c, 5c are attached to a side face of the processor unit 2 by means of a coupling cord 6, so that the caps 4c, 5c can be mounted to the connector receivers 4b, 5b to which the connectors are not connected.

However, in this manner of simply mounting the caps 4c, 5c to the connector receivers 4b, 5b, there is such a problem that the caps 4c, 5c may be forgotten to be mounted, or the caps 4c, 5c may be detached due to incomplete mounting. In such cases, electrical safety with respect to an internal circuit cannot be secured, and such anxiety that the user may get in touch with the electrode such as the pin in the connector receivers 4b, 5b cannot be excluded.

SUMMARY OF THE INVENTION

The invention has been made in view of the above described problems, and it is an object of the invention to provide an electronic endoscope apparatus in which electrical safety of an internal circuit can be secured, and such possibility that a user may get in touch with an electrode in a connector receiver can be eliminated, even in case where a cap is forgotten to be mounted to the connector receiver or incompletely mounted.

In order to attain the above described object, according to a first aspect of the invention, there is provided an observed image forming apparatus comprising: an apparatus body including a plurality of connector receivers to which electric connectors of a plurality of observation devices for obtaining an image of an object to be observed can be connected; a cap that is to be mounted to one of said plurality of connector receivers to which any of said plurality of electric connectors is not connected; and a cap insertion and extraction detecting circuit that detects whether or not the cap is mounted to the one of the connector receivers in the apparatus body, wherein, when mounting of the cap has been detected by the cap insertion and extraction detecting circuit, one of the observation devices an electric connector of which is connected to the other one of the connector receivers in the apparatus body is controlled to be driven.

According to second aspect of the invention, there is provided the observed image forming apparatus, wherein the cap insertion and extraction detecting circuit comprises: an insertion detecting circuit that detects insertion of the cap; and a pin connection detecting circuit that detects pin connection between the cap and the one of the connector receivers, and wherein the mounting of the cap is judged when the insertion of the cap has been detected by the insertion detecting circuit, and the pin connection has been detected by the pin connection detecting circuit.

According to the first aspect of the invention, only when the mounting of the cap has been detected by the cap insertion and extraction detecting circuit, power is supplied to the observation device such as the scope (electronic endoscope) and the ultrasonic probe, for example, and the obtained image is displayed on a monitor or the like. In short, unless the cap is mounted, the image will not be displayed.

According to the second aspect of the invention, only when the insertion of the cap has been detected by the insertion detecting circuit such as a photo-interrupter, and the pin connection between the cap (the cap provided with a short-circuited electrode) and the connector receiver has been detected by the pin connection detecting circuit, the observation device is driven. In this manner, the mounting of the cap can be confirmed through double detection.

BRIEF DESCRIPTION OF THE DRAWINGS

FIGS. 1A and 1B show a structure related to insertion and extraction of a cap to and from a connector receiver of an electronic endoscope apparatus which is an observed image forming apparatus in an embodiment according to the invention, in which FIG. 1A is a view showing a state before the cap is mounted, and FIG. 1B is a view showing a state after the cap has been mounted;

FIGS. 5A and 5B show structures of the related-art electronic endoscopes, in which FIG. 5A is a perspective view in case where a scope of type A is used, and FIG. 5B is a perspective view in case where a scope of type B is used.

DETAILED DESCRIPTION OF THE INVENTION

Figure 1A:
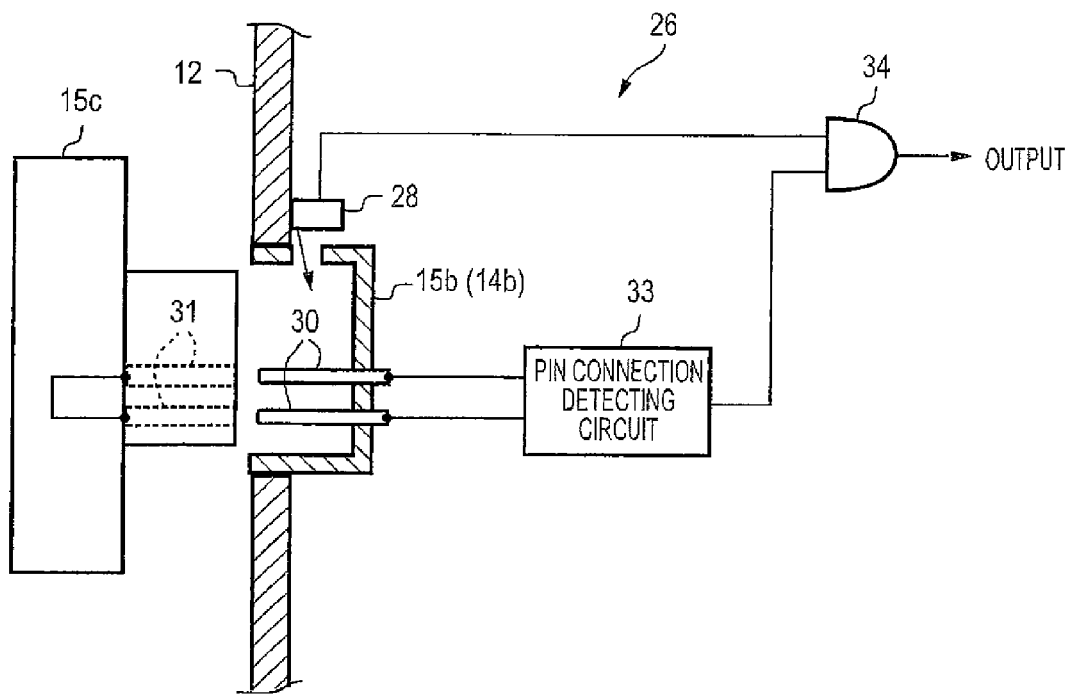
Figure 1B:
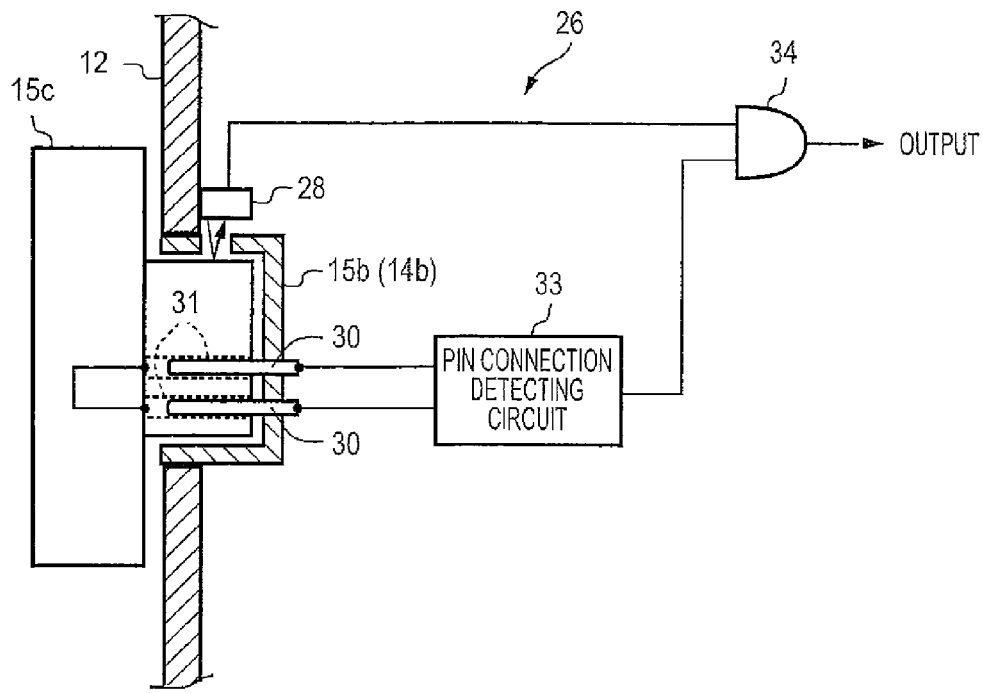
Figure 2:
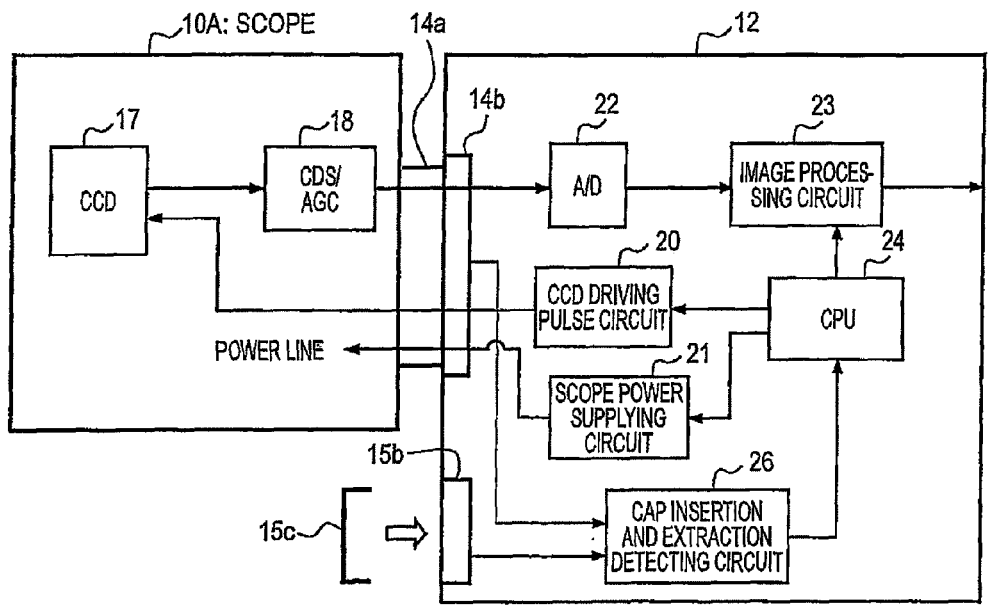
FIG. 2 is a block diagram showing an overall structure of the electronic endoscope apparatus in the embodiment.

FIGS. 1A, 1B and 2 show a structure of an electronic endoscope apparatus which is an observed image forming apparatus in an embodiment according to the invention. FIGS. 1A and 1B show a structure related to insertion and extraction of a cap into and from a connector receiver of a processor unit, and FIG. 2 shows an overall structure of the electronic endoscope apparatus. In the beginning, as shown in FIG. 2, in the electronic endoscope apparatus, a connector 14a of a scope 10A of type A (an observation device—an electronic endoscope) is connected to a connector receiver 14b of a processor unit (an apparatus body) 12, and this processor unit 12 is provided with a connector receiver 15b for connecting another scope of type B. The scope 10A contains therein a CCD 17 which is a solid body photographing element, a CDS (correlation double sampling)/AGC (auto gain control) circuit 18 for inputting an image taking signal which has been obtained by this CCD 17, and so on.

On the other hand, the processor unit 12 contains therein a CCD driving pulse circuit 20 for driving the CCD 17, a scope power supplying circuit 21 for supplying necessary power to the scope 10A, an A/D converter 22 for inputting an output of the CDS/AGC circuit 18, an image processing circuit 23 which performs a determined image processing of the output signal of this A/D converter 22, and a CPU (or a microcomputer) 24 which totally controls these circuits and also controls insertion and extraction of the cap.

In this embodiment, there is provided a cap (in a round shape, for example) 15c which is mounted and connected to the aforesaid connector receiver 15h (as for the other connector receiver 14b, a cap in a square shape for example is provided), and at the same time, a cap insertion and extraction detecting circuit 26 is connected to the connector receivers 14b, 15b.

A structure related to the cap 15c, the connector receiver 15h and the cap insertion and extraction detecting circuit 26 is shown in FIGS. 1A and 1B. A photo-interrupter (an insertion detecting circuit) 28 for detecting an inserted state of the cap 15c is provided on a side face of the connector receiver 15b. This photo-interrupter 28 has a light emitting part (such as a light emitting diode) and a light receiving part (a photo-transistor), and can detect the inserted state of the cap 15c with respect to the connector receiver 15b, by reflecting a light emitted from the light emitting part from the side face of the cap 15c, and by detecting the reflected light in the light receiving part.

A plurality of pins (electrodes) 30 are arranged in the connector receiver 15b, while two pin receivers (electrodes) 31 are provided in the cap 15c (arrangement of these pins and pin receivers may be reversed or some other structures may be employed). These pin receivers 31 make short circuits inside. Moreover, the connector receiver 15b is provided with a pin connection detecting circuit 33 for detecting connection between the pins 30 and the pin receivers 31, and an AND circuit 34 is provided on an after stage of the pin connection detecting circuit 33 and the aforesaid photo-interrupter 28.

Specifically, in the cap insertion and extraction detecting circuit 26 in this embodiment, when the cap 15c is mounted to the connector receiver 15b, as shown in FIG. 1B from the state as shown in FIG. 1A, the insertion of the cap 15c itself is detected by the photo-interrupter 28, and the connection between the pins 30 and the pin receivers 31 is also detected by the pin connection detecting circuit 33. At this moment only, a signal (High signal) for judging that the cap 15c has been mounted (mounting of the cap) is issued.

Figure 4:
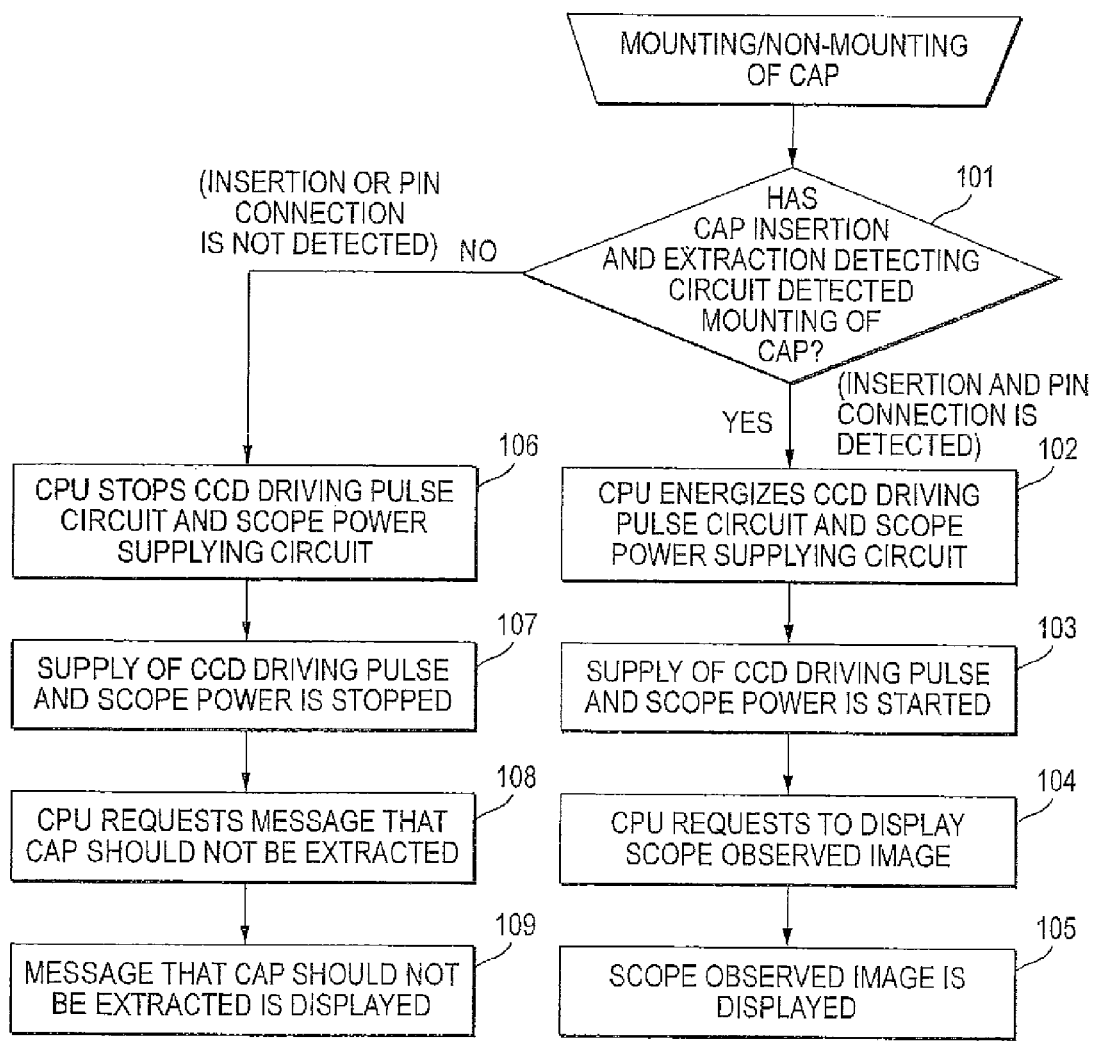
FIG. 4 is a flow chart showing operation related to mounting/non-mounting of the cap in the electronic endoscope in the embodiment.
Figure 5A:
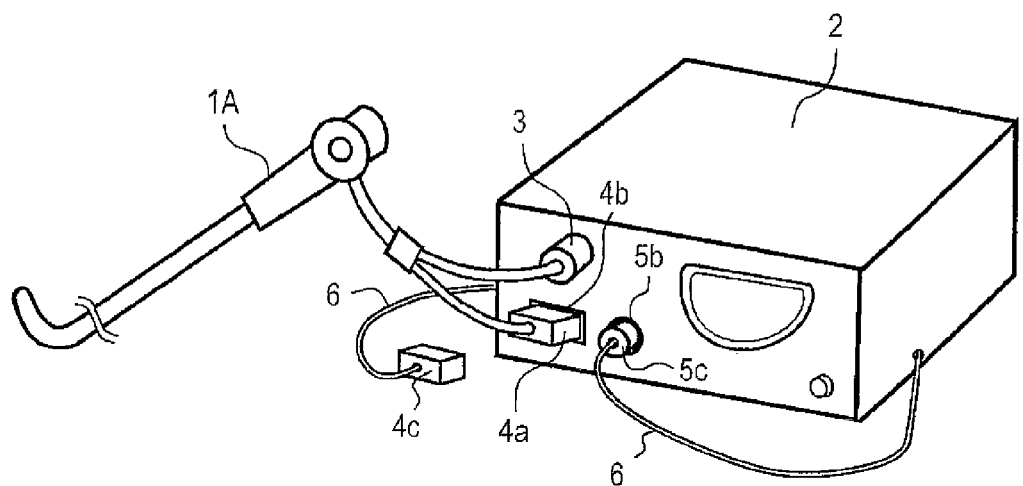
Figure 5B:
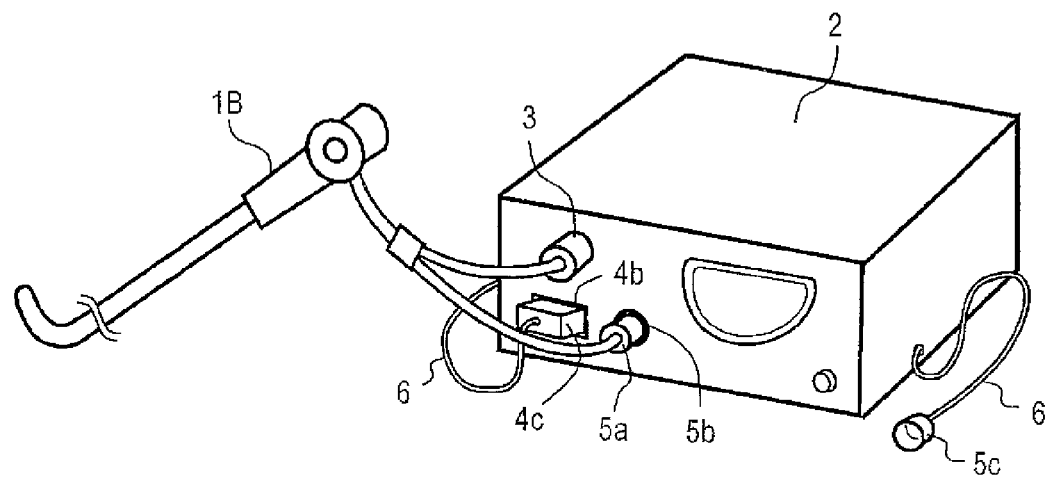

This embodiment has the above described structure, and the electronic endoscope apparatus in this embodiment is so constructed that a plurality of the scopes 10A or the like can be connected to the processor unit 12, as described referring to FIGS. 5A and 5B. For example, in case where the connector 14a of the scope 10A is connected to the connector receiver 14b of the processor unit 12, as shown in FIG. 2, the cap 15c is mounted to the other connector receiver 15b. On this occasion, operation as shown in FIG. 4 is performed in this embodiment.

In FIG. 4, when the mounting of the cap 15c has been performed as described above, it is judged in step 101 whether or not the cap insertion and extraction detecting circuit 26 has detected the insertion of the cap 15c. Then, as described referring to FIG. 1B, when the insertion of the cap 15c has been detected by the photo-interrupter 28, and the connection between the pins (30, 31) has been detected by the pin connection detecting circuit 33, it is judged that the cap 15c has been mounted (YES). Then, in step 102, the CPU 24 energizes the CCD driving pulse circuit 20 and the scope power supplying circuit 21, whereby supply of CCD driving pulse and supply of scope power to the CCD 17 of the scope 10A is started (step 103). Then, in step 104, the CPU 24 requests to display an image observed by the scope, and a determined signal processing is performed on an image signal which has been inputted from the scope 10A, in the image processing circuit 23, and the observed image is displayed on a monitor (step 105).

On the other hand, in case where the cap 15c is not yet mounted, has been detached or has been extracted, as shown in FIG. 1A, the insertion of the cap 15c is not detected by the photo-interrupter 28 (non-insertion is detected), the connection of the pins is not detected by the pin connection detecting circuit 33 (non-connection is detected) or both are not detected in the aforesaid step 101, and it is judged that the cap 15c is not mounted (NO). In this case, the CPU 24 stops the CCD driving pulse circuit 20 and the scope power supplying circuit 21 in step 106, and therefore, supply of the CCD driving pulse to the CCD 17 and supply of the scope power is stopped (107). Then, in step 108, the CPU 24 requests a message that the cap 15c should not be extracted, and the massage to the effect that the cap 15c should not be extracted is displayed on the monitor or the like (step 109).

In the above described cap insertion and extraction detecting circuit 26, only when the insertion of the cap 15c itself has been detected by the photo-interrupter 28 and the connection of the pin receivers 31 of the cap 15c to the pins 30 of the connector receiver 15b has been detected by the pin connection detecting circuit 33, the scope 10A is driven to operate. Therefore, through this double detection, forgetting to mount the cap 15c and incompletely mounting can be reliably prevented.

Figure 3:
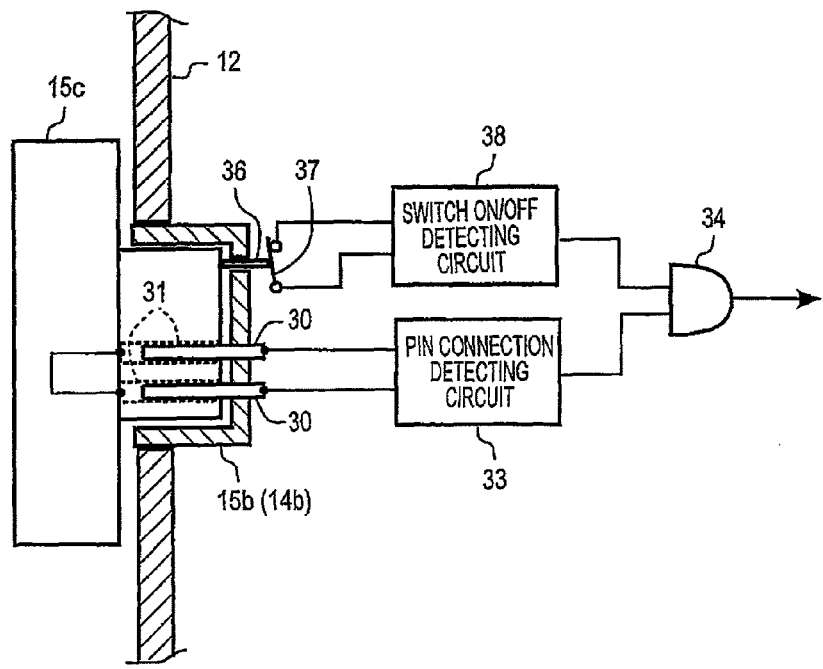
FIG. 3 is a view showing another example of a structure of an insertion detecting circuit in the embodiment.

FIG. 3 shows another example of the structure of the insertion detecting circuit in the cap insertion and extraction detecting circuit 26. In the insertion detecting circuit in this example, there are provided an operating rod 36 which is supported so as to reciprocally move to the right and left in the drawing, a micro switch 37 arranged at a back end side of this operating rod 36, and a switch on/off detecting circuit 38 for detecting of/off of the micro switch 37.

With the insertion detecting circuit in this structure, when the operating rod 36 is pushed by the insertion of the cap 15c, the micro switch 37 is turned on, whereby the insertion of the cap 15c is detected. Therefore, in the cap insertion and extraction detecting circuit 26, only when turning on of the micro switch 37 has been detected by this switch on/off detecting circuit 38, and the connection of the pins has been detected by the pin connection detecting circuit 33, an output of the AND circuit 34 becomes high. As the results, it is judged that the cap 15c has been mounted.

Although in the above described embodiment, it is so adapted that operation of the scope 10A starts, when the mounting of the cap 15c has been detected by the cap insertion and extraction detecting circuit 26, it is also possible to start operation of the processor unit 12 including the scope 10A, that is, operation of the electronic endoscope apparatus.

Moreover, although the invention is applied to the electronic endoscope apparatus in the embodiment, it is also possible to apply the invention to a complex observation apparatus in which a scope is connected to an ultrasonic probe, for example.

According to the observed image forming apparatus of the invention, there is obtained such advantage that electrical safety of the internal circuit can be secured, even in case where the cap is forgotten to be mounted, or incompletely mounted, and such possibility that a user may get in touch with the electrode inside the connector receiver can be eliminated.

Moreover, according to the second aspect of the invention, forgetting to mount the cap and incomplete mounting of the cap can be reliably prevented through the double detection.

The entire disclosure of each and every foreign patent application from which the benefit of foreign priority has been claimed in the present application is incorporated herein by reference, as if fully set forth.

What is claimed is:

1. An observed image forming apparatus comprising:
   an apparatus body including a plurality of connector receivers,
   wherein at least one connector receiver is connected to an electric connector of an observation device for obtaining an image of an object to be observed; and
   the other connector receivers are not connected to the electric connector of the observation device,
   a cap that is mounted to another connector receiver so as to prevent the electric connector of the observation device from connecting to the said another connector receiver; and
   a cap insertion and extraction detecting circuit that detects whether or not the cap is mounted to said another connector receivers in the apparatus body,
   wherein, when mounting of the cap has been detected by the cap insertion and extraction detecting circuit, the cap insertion and extraction detecting circuit issues a signal for judging that the cap has been mounted and the observation device which is connected to the one connector receiver is controlled to be driven in accordance with the signal.

2. An observed image forming apparatus as claimed in claim 1,
   wherein the cap insertion and extraction detecting circuit comprises: an insertion detecting circuit that detects insertion of the cap; and a pin connection detecting circuit that detects pin connection between the cap and the one of the connector receivers, and
   wherein the mounting of the cap is judged when the insertion of the cap has been detected by the insertion detecting circuit, and the pin connection has been detected by the pin connection detecting circuit.

* * * * *